United States Patent [19]

Morita et al.

[11] Patent Number: 5,117,035

[45] Date of Patent: May 26, 1992

[54] FLUORINE-CONTAINING ACRYLIC ACID DERIVATIVE AND POLYMER THEREOF

[75] Inventors: Shigeru Morita, Ikeda; Masahiko Oka, Ohtsu, both of Japan

[73] Assignee: Daikin Industries, Ltd., Osaka, Japan

[21] Appl. No.: 356,206

[22] Filed: May 24, 1989

Related U.S. Application Data

[60] Division of Ser. No. 20,133, Feb. 26, 1987, Pat. No. 4,943,653, which is a continuation of Ser. No. 751,724, Jul. 3, 1985, abandoned.

[30] Foreign Application Priority Data

Jul. 9, 1984 [JP] Japan ................................. 59-142986

[51] Int. Cl.$^5$ ..................... C07C 327/00; C07C 69/62; C07C 233/00
[52] U.S. Cl. .................................... 558/250; 558/256; 558/257; 560/26; 560/89; 560/90; 560/130; 560/185; 560/219; 562/887; 564/204
[58] Field of Search ................. 560/219, 185, 130, 26, 560/89, 90; 562/887; 564/204; 558/256, 257, 250

[56] References Cited

PUBLICATIONS

Tolman, V. et al Collect. Czech. Chem. Commun. 48(1) 319–26 1983.

*Primary Examiner*—Paul J. Killos
*Attorney, Agent, or Firm*—Birch, Stewart, Kolasch & Birch

[57] ABSTRACT

A novel fluorine-containing acrylic acid derivative of the invention is represented by the formula:

$$(CH_2=CF-CO)_p-A \qquad (I)$$

wherein A is a residue derived from an organic compound having at least two active hydrogen atoms derived by removing at least two active hydrogen atoms, and p is an integer corresponding to the valency of the residue A, which is easily cured.

4 Claims, No Drawings

FLUORINE-CONTAINING ACRYLIC ACID DERIVATIVE AND POLYMER THEREOF

This application is a divisional of copending application Ser. No. 07/020,133, filed on Feb. 26, 1987 U.S. Pat. No. 4,943,653 which is a continuation application of Ser. No. 06/751,724 filed Jul. 3, 1985 and now abandoned.

FIELD OF THE INVENTION

The present invention relates to a novel fluorine-containing acrylic acid derivative and a polymer thereof. More particularly, the present invention relates to a derivative of a novel α-fluoroacrylic acid and a homo- or co-polymer thereof.

DETAILED DESCRIPTION OF THE INVENTION

The novel fluorine-containing acrylic acid derivative of the present invention is represented by the formula:

$$(CH_2=CF-CO)_p-A \qquad (I)$$

wherein A is a residue derived from an organic compound having at least two active hydrogen atoms derived by removing at least two active hydrogen atoms, and p is an integer corresponding to the valency of residue A.

In the specification, the active hydrogen atom means a hydrogen atom bonded to an oxygen, sulfur or nitrogen atom, for example, a hydrogen atom included in water, an alcoholic hydroxyl group, a phenolic hydroxyl group, a carboxylic group, a primary and secondary amine group and a mercapto group.

In the formula (I), the residue A is preferably a group of the formula:

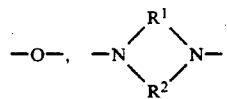

wherein $R^1$ and $R^2$ are, the same or different, a divalent organic group,

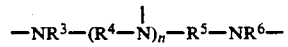

wherein $R^3$ and $R^6$ are, the same or different, a hydrogen atom or a monovalent organic group, $R^4$ and $R^5$ are, the same or different, a divalent organic group, and n is an integer not less than one (1), or

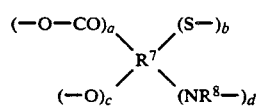

wherein $R^7$ is an organic group with (a+b+c+d) valencies, $R^8$ is a hydrogen atom or a monovalent organic group, and a, b, c and d are, the same or different, 0 or a positive integer and satisfy the equation: $a+b+c+d \geq 2$.

Specific examples of the residue A are as follows:

Residues derived from alcohols and phenols

—OCH$_2$CH$_2$O—,

—OCH$_2$CH(CH$_3$)O—,

—OCH$_2$CH$_2$CH(CH$_3$)O—,

—O(CH$_2$)$_4$O—,

—O(CH$_2$)$_6$O—,

—O(CH$_2$)$_2$(CF$_2$)$_2$(CH$_2$)$_2$O—,

—O(CH$_2$)$_2$(CF$_2$)$_4$(CH$_2$)$_2$O—,

—OCH$_2$C(CH$_3$)$_2$CH$_2$O—,

—(OCH$_2$CH$_2$)$_n$—OCH$_2$CH$_2$O—,

—[CH$_2$CH(CH$_3$)]$_n$—OCH$_2$CH(CH$_3$)O—,

—OCH$_2$C(CH$_3$)CH$_2$OCOC(CH$_3$)$_2$CH$_2$O—,

—O—(CH$_2$CH$_2$O)$_n$—CH$_2$CH$_2$O—,

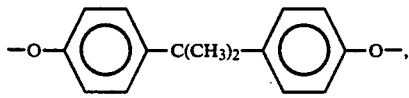

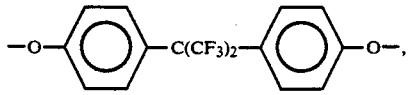

-continued
Residues derived from alcohols and phenols
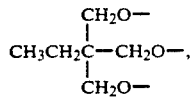
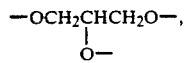
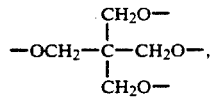
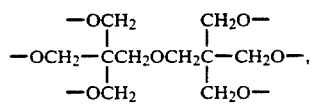
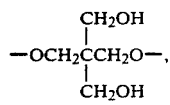
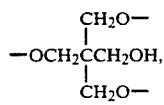
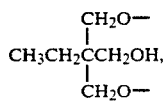
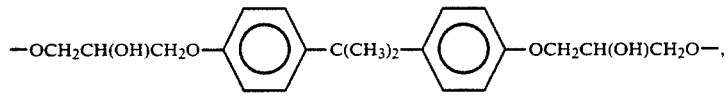
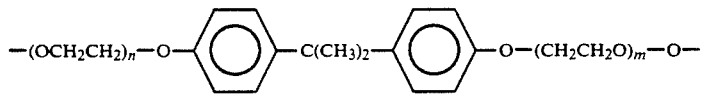
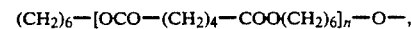
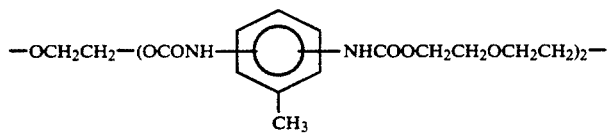
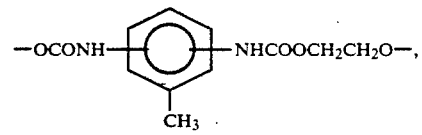

-continued
Residues derived from alcohols and phenols

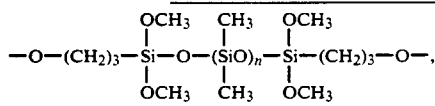

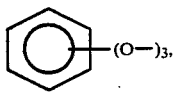

—OCH₂CH₂SCH₂CH₂O—, wherein l, m and n are each a positive integer.

Residues derived from amines
HN—(CH₂)$_d$—NH—
(wherein d is an integer of 2 to 12), —HN(CH₂CH₂NH)$_q$—CH₂CH₂NH—
(wherein q is 1 or 2),

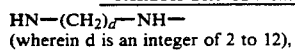

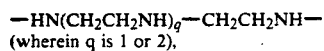

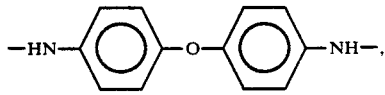

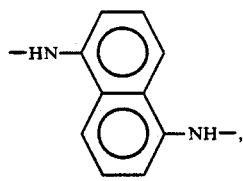

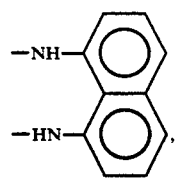

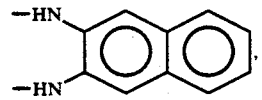

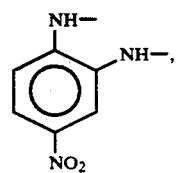

-continued
Residues derived from amines

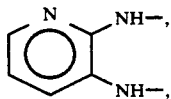

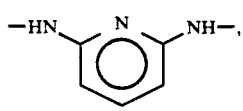

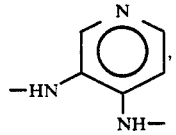

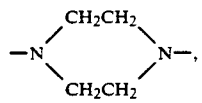

—(CH₂CH₂N)$_r$—
(wherein r is an integer of 2 or larger),

—OCH₂CH₂NH—,

—OCH₂CH₂NCH₂CH₂O—,

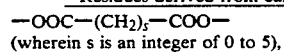

Residues derived from carboxylic acids
—OOC—(CH₂)$_s$—COO—
(wherein s is an integer of 0 to 5),

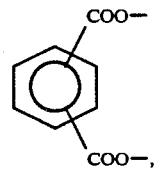

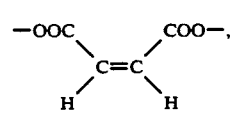

Residues derived from carboxylic acids
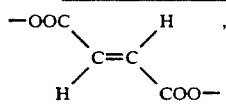
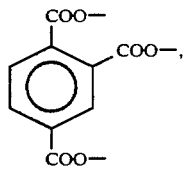
—OOC—C≡C—COO—,
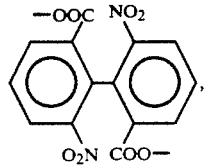
—OOCCH₂SCH₂COO—,
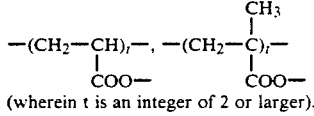
(wherein t is an integer of 2 or larger).
Residues derived from mercaptans
—SCH₂CH₂S—,
—SCH₂CH₂O—,
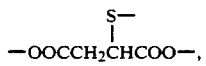
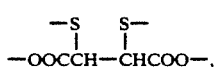
—SCH₂COO—,
—SCH₂CH₂COO—,
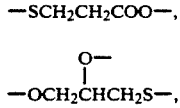
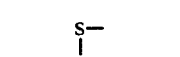
Residues derived from oxycarboxylic acids
—OCH₂COO—,
—OCH₂CH₂COO—,
—OCH(CH₃)COO—.
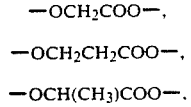
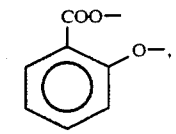
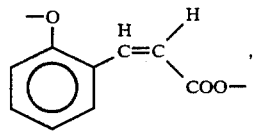
—OCH(COO—)₂,
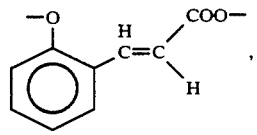
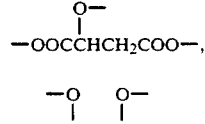
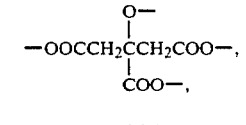
Residues derived from amino acids
—HNCH₂COO—,
—HNCH₂CH₂COO—,
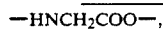
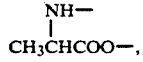
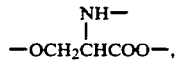
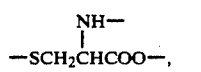

-continued
Residues derived from amino acids

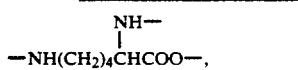

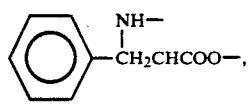

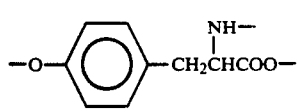

Residues derived from other compounds having active hydrogen atoms

—NCH$_2$SCH$_2$CHCOO—,

—HNCONH—,

—HNCSNH—.

Among the above residues, following are preferred:

—O—A'—O—
(wherein A' is a C$_{2-10}$ alkylene group or a polyoxy(C$_{2-3}$)alkylene with a degree of polymerization of 2 to 10).

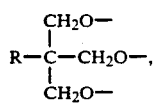

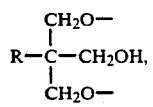

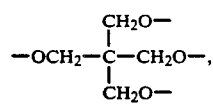

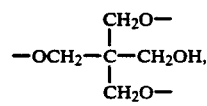

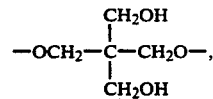

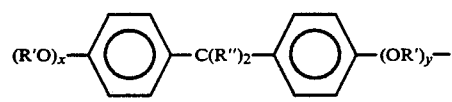

wherein R is a hydrogen atom or a C$_{1-5}$ alkyl group, R' is a single bond or a C$_{2-3}$ alkylene group, R" is a C$_{1-2}$ alkyl group or fluoroalkyl group, and x and y are each an integer of 1 to 20.

Specific examples of the fluorine-containing acrylic acid derivative of the present invention are as follows (in brackets, the state of the compound at room temperature under atmospheric pressure and the melting point determined as a temperature corresponding to an endothermic peak measured by DSC are shown.):

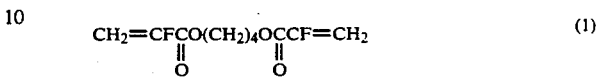 (1)

[Solid, 36.5° C.]

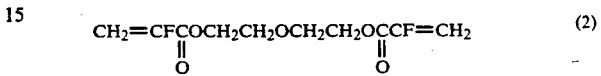 (2)

[Viscous liquid]

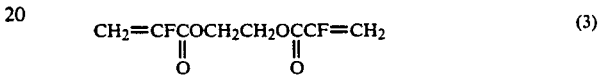 (3)

[Viscous liquid, 6.4° C.]

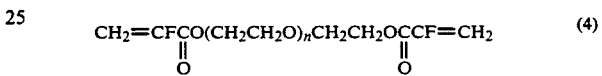 (4)

[Viscous liquid] (n averages about 10)

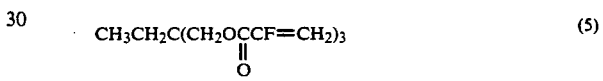 (5)

[Viscous liquid]

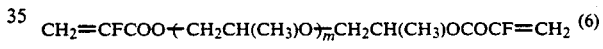 (6)

[Viscous liquid] (m averages about 17)

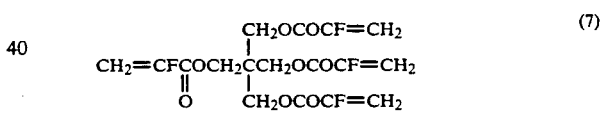 (7)

[White solid]

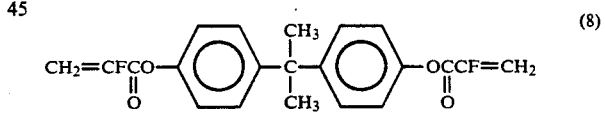 (8)

[White solid]

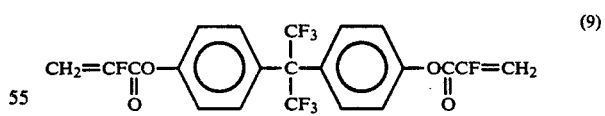 (9)

[Solid, 116.8° C.]

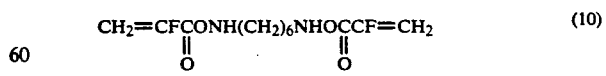 (10)

[Solid, 123° C.]

The fluorine-containing acrylic acid derivative (I) may be prepared as follows:

1. The compound having at least two active hydrogen atoms is reacted with an equimolar or excess amount of CH$_2$=CFCOF optionally in the presence of a solvent such as DMF, DMSO, acetone, acetonitrile and dioxane and an acid scavenger such as triethylamine.

2. The product is recovered by separation or by extraction with a suitable solvent such as dimethyl ether. Crystallizable derivatives (I) are recrystallized from, for example, petroleum benzine.

The fluorine-containing acrylic acid derivative (I) of the present invention is easily homo- or co-polymerized.

The liquid derivative (I) is polymerized as such while the solid one is polymerized by melting it or dissolving it in a suitable solvent. The polymerization is initiated and proceeded by heat or irradiation with UV light under atmospheric or reduced pressure or in an inactive gas atmosphere. Optionally, a polymerization initiator and/or a sensitizer may be used.

Two or more of the derivatives (I) may be copolymerized.

When the derivative (I) is copolymerized with an other monomer, examples of the copolymerizable monomer are as follows:

(meth)acrylic acid, (meth)acrylic halides, (meth)acrylic esters (e.g. methyl (meth)acrylate, ethyl (meth)acrylate, etc.), (meth)acrylic amides, (meth)arylonitrile, styrene and its derivatives (e.g. α-methylstyrene), vinyl ethers (e.g. methyl vinyl ether, ethyl vinyl ether, etc.), vinylpyridines, vinyl ketones (e.g. methyl vinyl ketone, ethyl vinyl ketone, divinyl ketone, etc.), vinyl chloride, vinylidene chloride, vinyl acetate, allyl chloride, olefines (e.g. ethylene, propene, butene, etc.), dienes (e.g. butadiene, etc.), fluorine-containing monomers (e.g. tetrafluoroethylene, trifluoroethylene, hexafluoropropylene, vinylidene fluoride, etc.), maleic acid and its anhydride, fumaric acid.

Since the fluorine-containing acrylic acid derivative (I) has at least two α-fluoroacrylic groups in a molecule, it is easily cured by heating or irradiation of light including UV light. The cure rate of the derivative (I), for example the fluorine-containing acrylic ester, is far larger than that of a corresponding acrylic ester not containing fluorine, which results in good processability. Furthermore, the fluorine-containing acrylic acid derivative (I) of the present invention is completely cured in air. The cured product has excellent heat resistance, oil resistance, etc. and may be used as a sheath material for glass optical fibers.

The fluorine-containing acrylic acid derivative (I) of the present invention is used as a printing plate, a resist material, a printing ink, a coating, an adhesive, a sealing material by making use of its curing characteristics. Particularly, it is used as a photosensitive printing plate and resist material, a UV curing printing ink, coating, adhesive and sealing. The derivative (I) is also used as a technical art material and a medical material.

The present invention will be hereinafter explained further in detail by following Examples.

EXAMPLE 1

Preparation of Compound (1)

In a flask, 1,4-butanediol (45 g) and dimethyl formamide (200 ml) were charged and then $CH_2=CFCOF$ (95 g) was dropwise added with stirring on an ice bath. After stirring the mixture for 10 hours, water (1,000 ml) was added, and a bottom layer was separated and washed with water three times. Then, the solution was cooled to precipitate crude crystal (108 g). The crude crystal (20 g) was added to petroleum benzine (200 ml) and warmed to dissolve the crystal. The solution was cooled to $-30°$ C. to recrystallize the compound, which was suction filtered, washed with petroleum benzine and dried to obtain a pure crystalline entitled product (18.4 g). Endothermic peak temperature in DSC, 36.5° C. In the thermogravimetric analysis, the product was cured during the raising the temperature and loss in weight started at 301.5° C.

| Elementary analysis: | C | H | F |
|---|---|---|---|
| Calc'd: | 51.29 | 5.17 | 16.22 |
| Found: | 50.57 | 3.76 | 15.76 |

EXAMPLE 2

Preparation of Compound (2)

In a flask, diethylene glycol (10 g), triethylamine (20 g) and acetone (60 ml) were charged, and $CH_2=CFCOF$ (21 g) was dropwise added with stirring on an ice bath. Then, the mixture was stirred for 5 hours and washed with water to obtain a viscous liquid entitled compound (21.2 g).

EXAMPLE 3

Preparation of Compound (4)

In a flask, polyethylene glycol (PEG #4000) (10 g), triethylamine (5 g) and dimethyl sulfoxide (10 ml) were charged, and $CH_2=CFCOF$ (15 g) was dropwise added with stirring on an ice bath. Then, the mixture was stirred for 5 hours, added with water and extracted with diethyl ether. The extract was dried under reduced pressure to obtain a viscous liquid entitled compound (10.8 g).

EXAMPLE 4

Preparation of Compound (5)

In a flask, trimethylolpropane (5 g) was dissolved in triethylamine (15 g), and $CH_2=CFCOF$ (20 g) was dropwise added with stirring on an ice bath. Then, the mixture was stirred for 5 hours, washed with water and dried to obtain a viscous liquid entitled compound (8 g).

EXAMPLE 5

Preparation of Compound (3)

In a flask, ethylene glycol (5 g) and triethylamine (5 g) were charged, and $CH_2=CFCOF$ (20 g) was dropwise added with stirring on an ice bath. Then, the mixture was stirred for 5 hours, washed with water and dried to obtain a viscous liquid entitled compound (14 g).

EXAMPLE 6

Preparation of Compound (6)

In a flask, polypropylene glycol (#1000) (20 g) and triethylamine (5 g) were charged, and $CH_2=CFCOF$ (8 g) was dropwise added with stirring on an ice bath. Then, the mixture was stirred for 5 hours, washed with water and dried to obtain a viscous liquid entitled compound (19 g).

EXAMPLE 7

Preparation of Compound (7)

In a flask, pentaerythritol (5 g) and dimethyl sulfoxide (20 ml) were charged, and $CH_2=CFCOF$ (30 g) was dropwise added with stirring on an ice bath. Then, the mixture was stirred for 5 hours, washed with water and recrystallized to obtain a white solid entitled compound (11 g).

EXAMPLE 8

Preparation of Compound (8)

In a flask, bisphenol-A (5 g), triethylamine (5 g) and dimethyl formamide (10 ml) were charged, and $CH_2=CFCOF$ (8 g) was dropwise added with stirring on an ice bath. Then, the mixture was stirred for 5 hours and recrystallized to obtain a white solid entitled compound (5.6 g).

EXAMPLE 9

Preparation of Compound (9)

In a flask, bisphenol-AF (5 g), triethylamine (5 g) and dimethyl formamide (10 ml) were charged, and $CH_2=CFCOF$ (8 g) was dropwise added on an ice bath. Then, the mixture was stirred for 5 hours and recrystallized to obtain a white solid entitled compound (4.1 g).

EXAMPLE 10

Polymerization of Compound (1)

Compound (1) was melted at 40° C., contained in a Pyrex (trade mark) glass tube with one end closed, evacuated and sealed. Then, sealed Compound (1) was cured within 10 seconds by irradiating with a 250 W extra-high pressure mercury lamp from a distance of 15 cm.

COMPARATIVE EXAMPLE 1

Polymerization of 1,4-butanediol diacrylate

In the same manner as in Example 10, 1,4-butanediol diacrylate was polymerized. Curing required 40 seconds.

EXAMPLE 11

Polymerization of Compound (1)

In the same manner as in Example 10 but conducting polymerization under atmospheric pressure and irradiating from a distance of 5 cm, Compound (1) was cured within 10 seconds.

COMPARATIVE EXAMPLE 2

Polymerization of 1,4-butanediol diacrylate

In the same manner as in Example 11, 1,4-butanediol diacrylate was polymerized. Curing required 90 seconds.

EXAMPLE 12

Copolymerization of Compound (1) and 1,4-butanediol diacrylate

In the same manner as in Example 10, Compound (1) and 1,4-butanediol diacrylate were copolymerized in a weight ratio of 1:1. Curing required 10 seconds.

EXAMPLE 13

Copolymerization of Compound (1) and 1,4-butanediol diacrylate

In the same manner as in Example 11, Compound (1) and 1,4-butanediol diacrylate were copolymerized in a weight ratio of 1:1. Curing required 25 seconds.

EXAMPLE 14

Copolymerization of Compound (1) and methyl acrylate

In the same manner as in Example 11, Compound (1) and methyl acrylate were copolymerized in a weight ratio of 1:1. Curing required 35 seconds.

COMPARATIVE EXAMPLE 3

Copolymerization of 1,4-butanediol diacrylate and methyl acrylate

In the same manner as in Example 11, 1,4-butanediol diacrylate and methyl acrylate were copolymerized in a weight ratio of 1:1. Curing required 155 seconds.

EXAMPLE 15

Copolymerization of Compound (1) and methyl methacrylate

In the same manner as in Example 11, Compound (1) and methyl methacrylate were copolymerized in a weight ratio of 1:1. Curing required 143 seconds.

COMPARATIVE EXAMPLE 4

Copolymerization of 1,4-butanediol diacrylate and methyl methacrylate

In the same manner as in Example 11, 1,4-butanediol diacrylate and methyl methacrylate were copolymerized in a weight ratio of 1:1. Curing required 210 seconds.

EXAMPLE 16

Compound (1) was contained in a glass tube and warmed on a water bath kept at a predetermined temperature and gel time was measured. The results are as follows:

| Temperature (°C.) | Gel time (min.) |
| --- | --- |
| 100 | 3 |
| 80 | 6 |
| 60 | 20 |
| 50 | 70 |

EXAMPLE 17

A solution of Compound (1) in dioxane in a predetermined concentration was contained in a glass tube and irradiated with a 250 W extra-high pressure mercury lamp from a distance of 15 cm and gel time was measured. The results are as follows:

| Concentration (%) | Gel time (min.) |
| --- | --- |
| 3.8 | >15 |
| 7.4 | 4 |
| 14.6 | 3 |

When a small amount of benzophenone or triethylamine was added as a sensitizer, Compound (1) gellated within one (1) minute.

EXAMPLE 18

Polymerization of Compound (2)

Compound (2) was coated on a surface of an aluminum plate and irradiated in air with a 250 W extra-high pressure mercury lamp from a distance of 15 cm for 5 minutes to obtain a hard coating.

COMPARATIVE EXAMPLE 5

Polymerization of diethylene glycol diacrylate

In the same manner as in Example 18, diethylene glycol diacrylate was coated on a surface of an aluminum plate and irradiated but was not cured.

EXAMPLE 19

Polymerization of Compound (4)

In the same manner as in Example 18, Compound (4) was coated on a surface of an aluminum plate and irradiated for 8 minutes to obtain a hard coating.

EXAMPLE 20

Polymerization of Compound (5)

In the same manner as in Example 18, Compound (5) was coated on a surface of an aluminum plate and irradiated for one (1) minute to obtain a hard coating.

EXAMPLE 21

Polymerization of Compounds (3), (6), (7), (8) and (9)

In the same manner as in Example 18, Compound (3), (6), (7), (8) or (9) was coated on a surface of an aluminum plate and irradiated to obtain a hard coating in a short time.

EXAMPLE 22

In a flask, hexamethylenediamine (2.54 g), pyridine (3.44 g) and dimethyl formamide (5 ml) were charged, and CH$_2$=CFCOF (3 ml) dissolved in dimethyl formamide (5 ml) was dropwise added with stirring on an ice bath. Then, the mixture was stirred for about one hour and poured in water (100 ml) to precipitate a pale yellow powdery entitled compound (4.8 g). M.P. 123° C.

A solution of the compound (0.1 g) in dimethyl formamide (0.6 g) was contained in a Pyrex (trade mark) glass tube and evacuated. Then, the compound was irradiated to start gellation within 13 minutes and completely cured within 19 minutes.

What is claimed is:

1. A fluorine-containing acrylic acid derivative of the formula:

(CH$_2$=CF—CO)$_p$—A wherein p corresponds to the valency of A, and A is a residue selected from the group consisting of:

(1) an amino group selected form the group consisting of:

—HN—(CH$_2$)$_4$—NH—

—HN(CH$_2$CH$_2$NH)$_q$—CH$_2$CH$_2$NH—

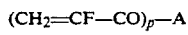

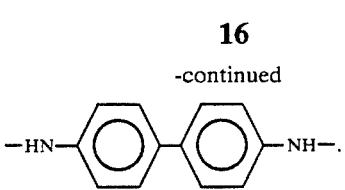

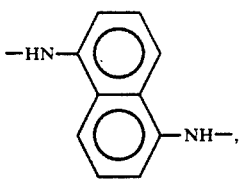

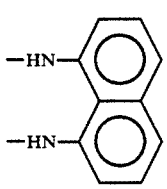

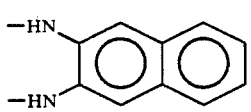

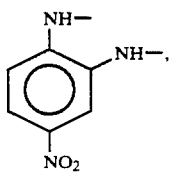

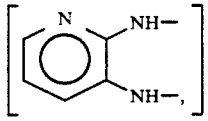

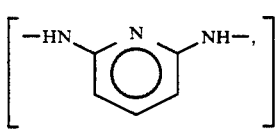

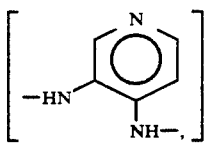

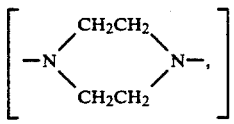

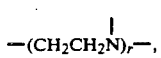

—(CH$_2$CH$_2$N)$_r$—,

—OCH$_2$CH$_2$NH—,

—OCH$_2$CH$_2$NCH$_2$CH$_2$O—,

-continued
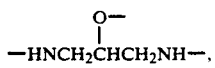
wherein d is an interger of 2 to 12, q is 1 or 2, and r is an integer greater than or equal to 2,
—HNCH₂COO—,
—HNCH₂CH₂COO—,
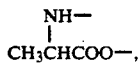
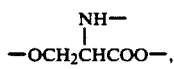
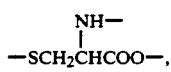
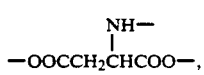
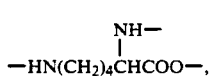
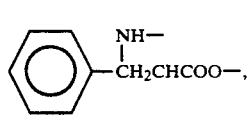
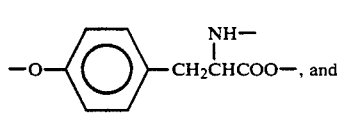
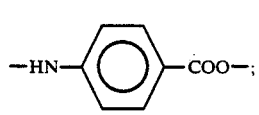
(2) a carboxylic group selected from the group consisting of:
—OOC—(CH₂)ₛ—COO—
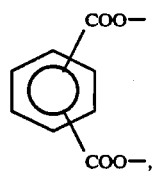
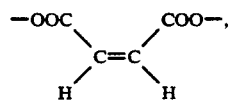
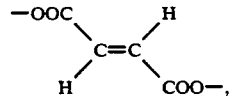
-continued
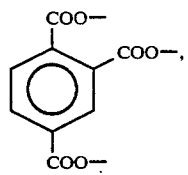
—OOC—C=C—COO—,
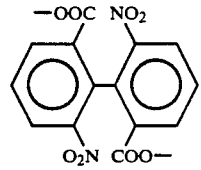
—OOCCH₂SCH₂COO—, and
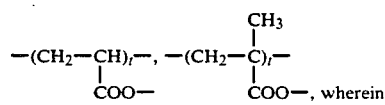
s is an integer of 0 to 5 and t is an integer greater than or equal to 2,
—OCH₂COO—,
—OCH₂CH₂COO—,
—OCH(CH₃)COO—,
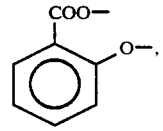
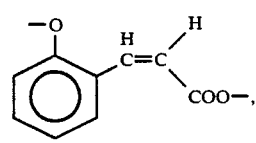
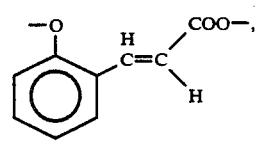
—OCH(COO—)₂,
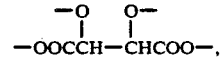
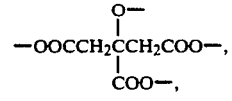

-continued

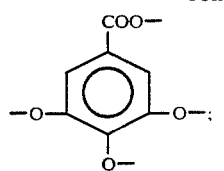

(3) a mercapto group selected from the group consisting of:

—SCH$_2$CH$_2$S—,

—SCH$_2$CH$_2$O—,

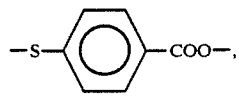

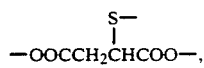

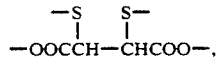

—SCH$_2$COO—,

—SCH$_2$CH$_2$COO—,

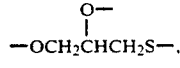

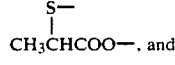, and

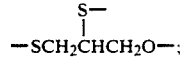;

and
(4) a phenol group selected from the group consisting of:

—OCH$_2$CH$_2$O—,

—OCH$_2$CH(CH$_3$)O—,

—OCH$_2$CH$_2$CH(CH$_3$)O—,

—O(CH$_2$)$_4$O—,

—O(CH$_2$)$_6$O—,

—O(CH$_2$)$_2$(CF$_2$)$_2$(CH$_2$)$_2$O—,

—O(CH$_2$)$_2$(CF$_2$)$_4$(CH$_2$)$_2$O—,

—OCH$_2$C(CH$_3$)$_2$CH$_2$O—,

—(OCH$_2$CH$_2$)$_n$—OCH$_2$CH$_2$O—,

—[CH$_2$CH(CH$_3$)]$_n$—OCH$_2$CH(CH$_3$)O—,

—OCH$_2$C(CH$_3$)CH$_2$OCOC(CH$_3$)$_2$CH$_2$O—,

-continued

—O—(CH$_2$CH$_2$O)$_n$—CH$_2$CH$_2$O—,

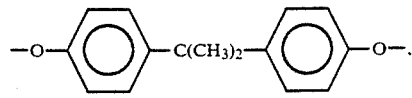

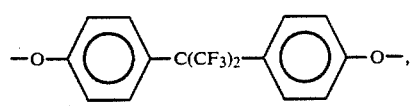

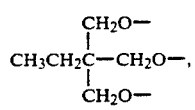

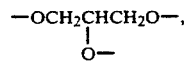

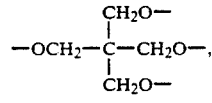

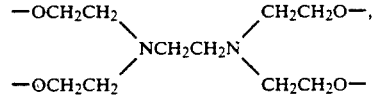

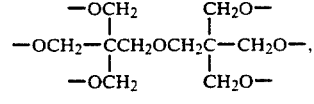

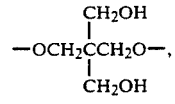

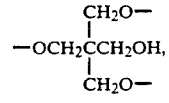

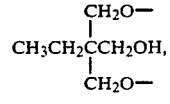

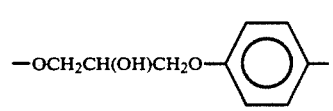

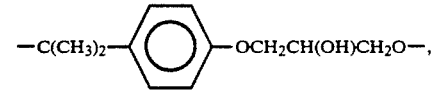

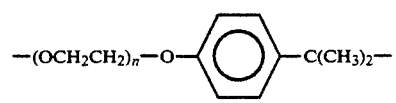

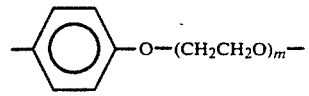

-continued

—O—(CH₂)₆—[OCO—(CH₂)₄—COO(CH₂)₆]ₙ—O—,

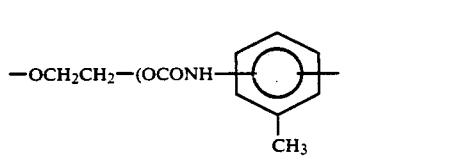

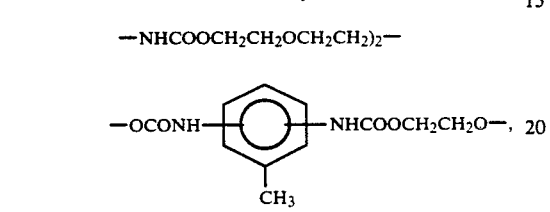

—NHCOOCH₂CH₂OCH₂CH₂)₂—

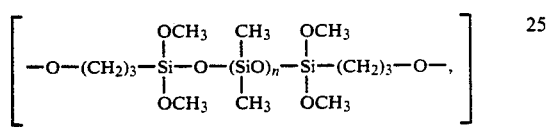

—OCH₂CH₂SCH₂CH₂O—, wherein l, m and n are each a positive integer.

2. A fluorine-containing acrylic acid derivative as recited in claim 1, wherein A is

—NH(CH₂CH₂NH)₂—CH₂CH₂NH—.

3. A fluorine-containing acrylic acid derivative as recited in claim 1, wherein the A residue in the formula (CH₂=CF—CO)ₚ—A is selected from the group consisting of:

—OCH₂CH₂O—,

—OCH₂CH(CH₃)O—,

—OCH₂CH₂CH(CH₃)O—,

—O(CH₂)₄O—,

—O(CH₂)₆O—,

—O(CH₂)₂(CF₂)₂(CH₂)₂O—,

—O(CH₂)₂(CF₂)₄(CH₂)₂O—,

—OCH₂C(CH₃)₂CH₂O—,

—(OCH₂CH₂)ₙ—OCH₂CH₂O—,

—[CH₂CH(CH₃)]ₙ—OCH₂CH(CH₃)O—,

—OCH₂C(CH₃)CH₂OCOC(CH₃)₂CH₂O—,

—O—(CH₂CH₂O)ₙ—CH₂CH₂O—,

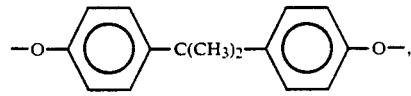

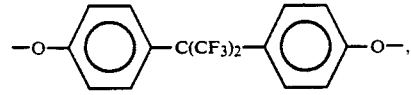

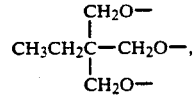

—OCH₂CHCH₂O—,
        |
        O—

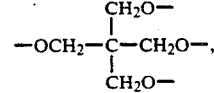

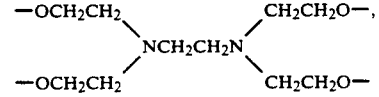

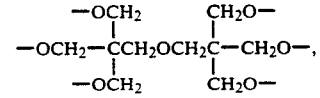

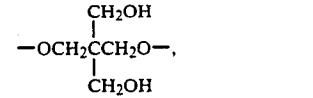

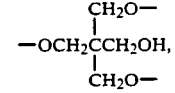

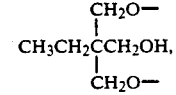

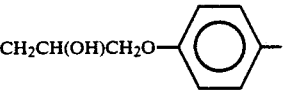

—O—(CH₂)₆—[OCO—(CH₂)₄—COO(CH₂)₆]ₙ—O—,

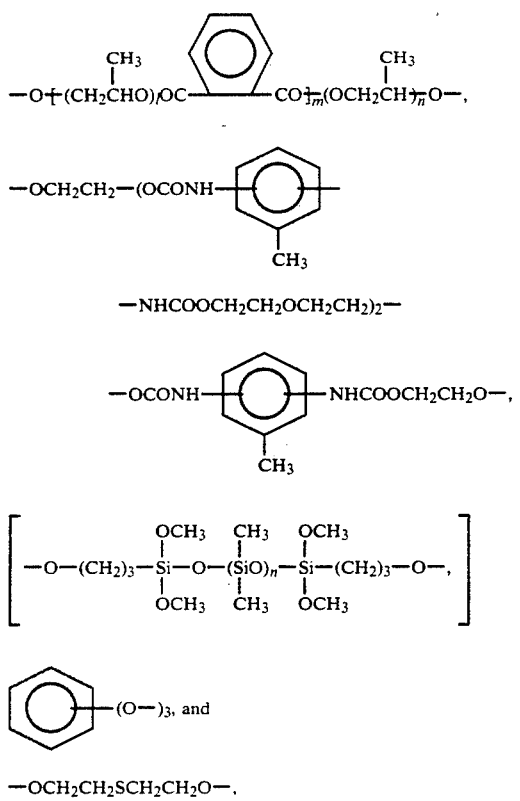
wherein l, m and n are each a positive integer.
4. A fluorine-containing acrylic acid derivative as recited in claim 1, wherein the A residue in the formula $(CH_2=CF-CO)_p-A$ is selected from the group consisting of:
—HN—$(CH_2)_d$—NH—
—HN$(CH_2CH_2NH)_q$—$CH_2CH_2NH$—
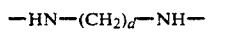
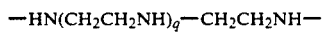
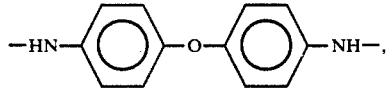
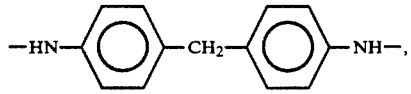
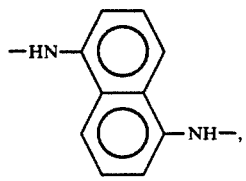
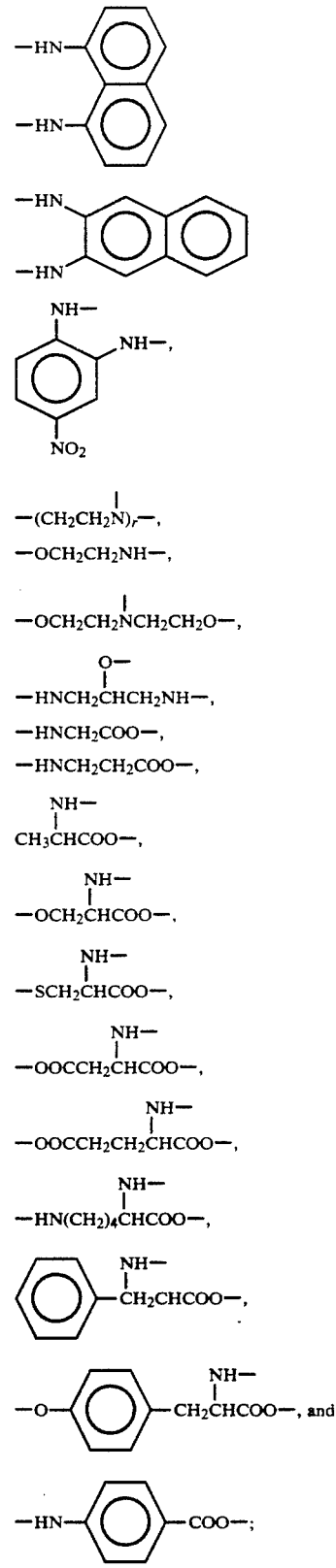
wherein d is an integer of 2 to 12, q is an integer of 1 to 2, and r is an integer of greater than or equal to 2.